US012560544B2

(12) United States Patent
Kercher et al.

(10) Patent No.: US 12,560,544 B2
(45) Date of Patent: Feb. 24, 2026

(54) ULTRABRIGHT FLUORESCENT NANOCOMPOSITE STRUCTURES FOR ENHANCED FLUORESCENT BIOASSAYS

(71) Applicant: Auragent Bioscience, LLC, St. Louis, MO (US)

(72) Inventors: Clare Kercher, St. Louis, MO (US); Qisheng Jiang, St. Louis, MO (US); Scott L. Crick, St. Louis, MO (US)

(73) Assignee: Auragent Bioscience, LLC, St. Louis, MO (US)

( * ) Notice: Subject to any disclaimer, the term of this patent is extended or adjusted under 35 U.S.C. 154(b) by 822 days.

(21) Appl. No.: 17/759,829

(22) PCT Filed: Jan. 29, 2021

(86) PCT No.: PCT/US2021/015750
§ 371 (c)(1),
(2) Date: Jul. 29, 2022

(87) PCT Pub. No.: WO2021/155181
PCT Pub. Date: Aug. 5, 2021

(65) Prior Publication Data
US 2023/0110606 A1 Apr. 13, 2023

Related U.S. Application Data

(60) Provisional application No. 62/968,314, filed on Jan. 31, 2020.

(51) Int. Cl.
B82Y 15/00 (2011.01)
B82Y 20/00 (2011.01)
(Continued)

(52) U.S. Cl.
CPC .......... G01N 21/6486 (2013.01); B82Y 30/00 (2013.01); G01N 21/648 (2013.01);
(Continued)

(58) Field of Classification Search
None
See application file for complete search history.

(56) References Cited

U.S. PATENT DOCUMENTS

2010/0135856 A1* 6/2010 Pyo ................. G01N 33/54346
422/69
2014/0017810 A1 1/2014 Kimura
(Continued)

FOREIGN PATENT DOCUMENTS

| CN | 101796416 A | 8/2010 |
| CN | 103370339 A | 10/2013 |

(Continued)

OTHER PUBLICATIONS

Lin Wang et al: "Fluorescence calibration research of microspheres in a microfluidic chip", Design for Manufacturability Through Design-Process Integration III , vol. 5718, Jan. 22, 2005 (Jan. 22, 2005), p. 272, XP55575505, 1000 20th St. Bellingham WA 98225-6705 USA ISSN: 0277-786X, DOI: 10.1117/12.591610 ISBN: 978-1-5106-2781-9.

(Continued)

*Primary Examiner* — Neil N Turk
(74) *Attorney, Agent, or Firm* — Polsinelli PC

(57) ABSTRACT

Described herein is a fluorescent nanocomposite. The fluorescent nanocomposite structure may include a plasmonic nanostructure comprising having at least one localized surface plasmon resonance wavelength ($\lambda$LSPR), at least one spacer coating, at least one fluorescent agent having a maximum excitation wavelength ($\lambda$EX), and at least one peptide-loaded major histocompatibility complex (MHC) molecule (pMHC). The fluorescent nanocomposite structure has a fluorescent intensity that is at least 500 times greater than a fluorescent intensity of the at least one fluorescent agent alone.

8 Claims, 11 Drawing Sheets

(51) Int. Cl.

| | | |
|---|---|---|
| *B82Y 30/00* | (2011.01) | |
| *G01N 21/64* | (2006.01) | |
| *G01N 33/533* | (2006.01) | |
| *G01N 33/542* | (2006.01) | |
| *G01N 33/543* | (2006.01) | |

(52) U.S. Cl.
    CPC ......... *G01N 33/533* (2013.01); *G01N 33/542* (2013.01); *G01N 33/54346* (2013.01)

(56) References Cited

U.S. PATENT DOCUMENTS

| | | |
|---|---|---|
| 2014/0030821 A1 | 1/2014 | Ohtsuka |
| 2014/0057805 A1 | 2/2014 | Tinnefeld et al. |
| 2014/0271889 A1 | 9/2014 | Messersmith et al. |
| 2015/0080248 A1 | 3/2015 | Tao et al. |
| 2016/0228549 A1 | 8/2016 | Messersmith et al. |
| 2016/0355567 A1 | 12/2016 | Wong et al. |
| 2019/0367966 A1 | 12/2019 | Belhocine et al. |

FOREIGN PATENT DOCUMENTS

| | | | |
|---|---|---|---|
| JP | 2010197746 A | 9/2010 | |
| JP | 2012-211799 A | 11/2012 | |
| WO | 2011096394 A1 | 8/2011 | |
| WO | WO-2013172942 A1 * | 11/2013 | .............. G01N 1/34 |
| WO | 2019/149932 A1 | 8/2019 | |
| WO | WO-2020072924 A1 * | 4/2020 | ....... G01N 33/54373 |

OTHER PUBLICATIONS

Mario Raab et al: "Using DNA origami nanorulers as traceable distance measurement standards and nanoscopic benchmark structures", Scientific Reports, vol. 8, No. 1, Jan. 29, 2018 (Jan. 29, 2018), XP55575522, DOI: 10.1038/s41598-018-19905-x.

Virpi Korpelainen et al: ""DNA origamistructures as calibration standards for nanometrology"", Measurement Science and Technology, IOP, Bristol, GB, vol. 28, No. 3, Jan. 23, 2017 (Jan. 23, 2017), p. 34001, XP020313856, ISSN: 0957-0233, DOI: 10.1088/1361-6501/28/3/034001 [retrieved on Jan. 23, 2017].

Ingo H. Stein et al: "Single-Molecule FRET Ruler Based on Rigid DNA Origami Blocks", ChemPhysChem—A European Journal of Chemical Physics & Physicalchemistry., vol. 12, No. 3, Feb. 25, 2011 (Feb. 25, 2011), pp. 689-695, XP55574486, DE ISSN: 1439-4235, DOI: 10.1002/cphc.201000781.

Yuan et al., "Thousand-fold Enhancement of Single-Molecule Fluorescence Near a Single Gold Nanorod", Angewandte Chemie, vol. 125, Issue 4, URL:https://onlinelibrary.wiley.com/doi/abs/10.1002/anie.201208125, Dec. 6, 2012 (Dec. 6, 2012).

Office Action issued for Canadian Application No. 3,165,161 dated Nov. 14, 2023 (5 Pages).

International Search Report for PCT/US2021/015750, dated Apr. 28, 2021, 08 pages.

Asselin Jeremie et al., "Metal-Enhanced Fluorescence and FRET in Multilayer Core-Shell Nanoparticles", Advances in Chemistry, vol. 2014, 812313, Jun. 9, 2014, pp. 1-16.

Fothergill Sarah Madeline et al., "Metal Enhanced Fluorescence Biosensing: From Ultra-Violet towards Second Near-Infrared Window", Nanoscale, vol. 10, No. 45, Nov. 22, 2018, pp. 20914-20929.

Wang Line et al., "Multicolor FRET Silica Nanoparticles by Single Wavelength Excitation", Nano Letters, vol. 6, No. 1, Dec. 20, 2005, pp. 84-88.

Extended Search Report for European Application No. 21747108.5, dated Apr. 24, 2024 (12 Pages).

Office Action for Chinese Application No. 202180011149.8, dated Jul. 24, 2025, 8 pages.

Office Action for Japanese Application No. 2022-546721, Sep. 9, 2024, 6 pages.

Office Action for Japanese Application No. 2022-546721, Mar. 17, 2025, 4 pages.

Laugel, B., et al., "Design of soluble recombinant T cell receptors for antigen targeting and T cell inhibition," Journal of Biological Chemistry, Feb. 2005, 43 pages.

Wooldridge, L., et al., "Tricks with tetramers: how to get the most from multimeric peptide-MHC," Immunology, 5 2009, vol. 126, pp. 147-164.

* cited by examiner

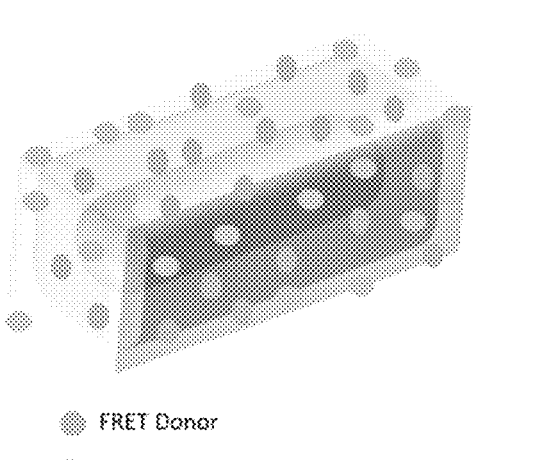

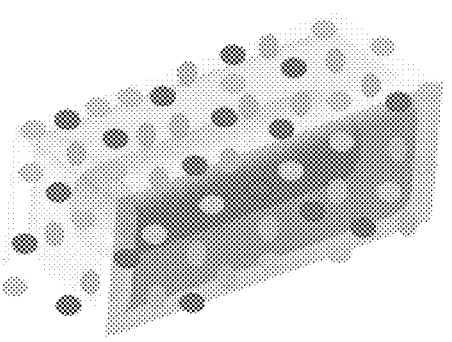

● FRET Donor

● FRET Acceptor

Excitation of Donor fluorophore will cause emission of Acceptor fluorophore, with emission of Donor fluorophore significantly reduced.

● FRET Donor1

● FRET Acceptor1/FRET Donor2

● FRET Acceptor2

Excitation of Donor1 fluorophore will cause emission of Acceptor2 fluorophore, with emission of Donor1 and Acceptor1/Donor2 fluorophores significantly reduced.

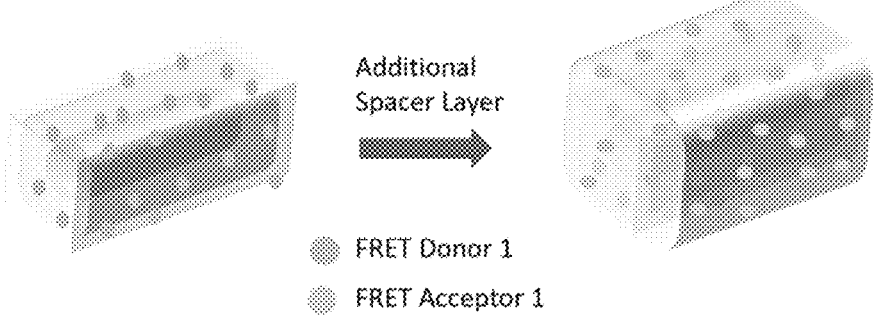

Additional Spacer Layer

● FRET Donor 1

● FRET Acceptor 1

Instead of conjugating the FRET dyes on same spacer layer, dyes can also be conjugated to multiple spacer layers. For example, FRET Donor 1 is conjugated to a spacer that is ideally 2-5 nm thick and then a second spacer layer that is 1-3 nm thick is added. FRET Acceptor 1 is conjugated to this second spacer layer.

Figure 7

Add Plasmonic-
Fluor to solution of
biotinylated pMHC

🦴 MHC Heavy Chain    🦴 Peptide    ● Biotin    ◉ β2M    Streptavidin-coated plasmonic-fluor

ULTRABRIGHT FLUORESCENT NANOCOMPOSITE STRUCTURES FOR ENHANCED FLUORESCENT BIOASSAYS

CROSS-REFERENCE TO RELATED APPLICATIONS

This application claims priority to U.S. Patent Application Ser. No. 62/968,314, filed on Jan. 31, 2020, the entire contents of which are hereby incorporated by reference.

FIELD

The present disclosure is directed to ultrabright fluorescent nanocomposite structures for enhanced fluorescent bioassays.

BACKGROUND

Detection and quantification of various biomolecules in biological fluids and tissues is of fundamental importance in biomedical research and clinical diagnostics because it is impossible to fully characterize complex, non-linear, biochemical systems without being able to accurately and quantitatively interrogate the component molecules. This problem is ubiquitous across all domains of biomedical research, and it is a major barrier to fully understanding health, ageing, and disease. The problem is not a trivial one, especially for proteins and peptides which do not have amplification schemes like PCR for nucleic acids, because relevant concentrations of molecules related to diseases like cancer, heart disease, and neurodegeneration can range in concentration many orders of magnitude from fg/mL levels to mg/mL. Even the same molecule can vary in abundance by orders of magnitude depending on the physiological state (e.g. health vs. disease) or the sample milieu (e.g. blood vs. cerebrospinal fluid). Finally, of particular importance to the research community, samples are incredibly precious and sometimes extremely limited in the amount available. Fluorescence probes and fluorometric approaches have been employed in biomedical research, not only as imaging tools to visualize the location and dynamics of cells and various sub-cellular species and molecular interactions in cells and tissues, but also as labels/reporters in fluoroimmunoassays for detection and quantification of molecular biomarkers. Fluorescence-based techniques have radically transformed biology and life sciences by unravelling the genomic, transcriptomic, and proteomic signatures of disease development, progression, and response to therapy. However, "feeble signal" has been a persistent and recurring problem in a battery of detection and imaging techniques that rely on fluorescence. All fluorescence-based bioanalytical techniques are ultimately limited in their detection sensitivity by the amount of light that can be collected during the interrogation period from an individual fluorescent species which serves as a reporter. Generally, weak fluorescence signal from individual reporter fluorophores and the associated poor signal-to-noise ratio limits the ultimate sensitivity of current fluorescence-based assays.

One approach to address this problem is to improve the detection instrumentation by using more sensitive detectors coupled with a higher numerical aperture optical system. The downsides of this approach are: 1) the great expense of the detection instrumentation and optical system; and 2) the higher numerical aperture results in a significantly limited field-of-view, making assay readout extremely long. More-over, typical fluorophores used in bioassays only have a limited useable lifetime over which they can emit photons before they photobleach.

While fluorescence provides a number of benefits (including multiplexing, high dynamic range, broad platform applicability (i.e. can be used in cells, on cells, tissues, plates, beads, solution, etc.)) over assay detection schemes such as colorimetric ELISA or chemiluminescence, fluorescence is fundamentally limited by poor signal. In plate-based assays, complicated schemes are employed like poly-HRP, PCR-ELISA, avidin-biotin-complex (ABC) ELISA, and tyramide signal amplification (TSA) to achieve improved fluorescence detection sensitivity. All of these are more complicated, more expensive, and generally have poorer dynamic range than the version of the assay they replace. For very high detection sensitivities, complicated technologies such as digital ELISA (Quanterix Simoa System) or electrochemiluminescence (Meso Scale Discovery) each require specialized substrates, equipment, and workflows.

In spectrally multiplexed fluorescent assays wherein distinct species are labeled with spectrally distinct fluorescent probes, the more unique fluorophores available, the more highly multiplexed an assay can be. In particular, it is important to have unique combinations of excitation and emission spectra.

BRIEF SUMMARY

In one aspect, disclosed herein is a fluorescent nanoconstruct structure comprising a plasmonic nanostructure having at least one localized surface plasmon resonance wavelength ($\lambda$LSPR), at least one spacer coating, at least one fluorescent agent having a maximum excitation wavelength ($\lambda$EX), and at least one peptide-loaded major histocompatibility complex (MHC) molecule (pMHC). The fluorescent nanocomposite structure has a fluorescent intensity that is at least 500 times greater than a fluorescent intensity of the at least one fluorescent agent alone.

In some aspects, the nanoconstruct may comprise a silver-coated gold nanorod (AuNR@Ag) plasmonic nanostructure having at least one localized surface plasmon resonance wavelength ($\lambda$LSPR) greater than 350 nm, at least one spacer coating, at least one fluorescent agent having a wavelength where it is maximally excited ($\lambda$EX), and at least one biorecognition element. The gold nanorod (AuNR) used to form the AuNR@Ag has at least one localized surface plasmon resonance wavelength greater than 650 nm before coating with silver. The fluorescent nanoconstruct has a fluorescence intensity that is at least 500 times greater than the fluorescence intensity of the at least one fluorescent agent alone under similar illumination and detection conditions.

In one aspect, disclosed herein is a method for making a fluorescent nanoconstruct. The method comprises, generally, providing AuNR@Ag plasmonic nanostructure wherein the gold nanorod (AuNR) used to form the AuNR@Ag has at least one localized surface plasmon resonance wavelength greater than 650 nm; coating the AuNR@Ag plasmonic nanostructure with at least one spacer coating, conjugating at least one fluorescent agent to the spacer coating; coating the spacer layer with a functional layer; and conjugating a biorecognition element to one of the at least one spacer coating or the functional layer.

In an aspect, further disclosed herein is a fluorescent nanocomposite structure comprising a plasmonic nanostructure having at least one localized surface plasmon resonance wavelength ($\lambda$LSPR), at least one spacer coating, at least one fluorescent agent having a first maximum excitation wavelength ($\lambda$EX1) and a first maximum emission wavelength ($\lambda$EM1), and at least one fluorescent agent having a second maximum excitation wavelength ($\lambda$EX2) and a second maximum emission wavelength ($\lambda$EM2). The fluorescent nanocomposite structure can be excited with light at $\lambda$EX1 and can emit light at $\lambda$EM2, and an intensity of emission at $\lambda$EM2 is greater than an intensity of emission at $\lambda$EM1.

In one aspect disclosed herein is a fluorescent nanoconstruct having a long Stokes shift. The nanoconstruct generally comprises a plasmonic nanostructure having at least one localized surface plasmon resonance wavelength ($\lambda$LSPR), at least one spacer coating, and at least one fluorescent agent serving as a Forster Resonance Energy Transfer (FRET) donor having a wavelength where it is maximally excited ($\lambda$EX_D) and at least one fluorescent agent serving as a FRET acceptor with a wavelength where it maximally emits ($\lambda$EM_A); wherein the fluorescent agent serving as the FRET donor has a $\lambda$EX_D within 50 nm at least one of the $\lambda$LSPR of the plasmonic nanostructure; and wherein the fluorescent nanoconstruct can be excited at $\lambda$EX_D and emit light at $\lambda$EM_A.

In one aspect disclosed herein is fluorescent nanoconstruct functionalized with multiple peptide-MHC (pMHC) molecules and capable of recognizing T-cell antigen receptors (TCRs) specific to the peptide bound to the MHC. The fluorescent construct functionalized with pMHC is allows significantly higher detection sensitivity compared to the current standard fluorescent reagent, pMHC bound to fluorescently labeled streptavidin. This is due to the fact that the fluorescent nanoconstruct disclosed herein allows conjugation of more than four MHC molecules per complex, unlike fluorescent streptavidin, and is significantly brighter than a streptavidin labeled with a spectrally equivalent fluorophore. The pMHC-decorated fluorescent nanoconstruct disclosed herein can attach to multiple TCRs even if they are present at a low cell-surface density.

In another aspect disclosed herein is a method of identifying T-cells with specific T-cell receptors. The method may include providing a sample containing T-cells, contacting the sample containing T-cells with a fluorescent nanocomposite structure comprising at least one major histocompatibility complex (MHC) molecule loaded with a peptide (pMHC) that can specifically bind to T-cells containing receptors specific to the peptide, spatially separating the T-cells, exciting the fluorescent nanocomposite structure with a wavelength of light that will induce fluorescence emission, and detecting the T-cells that are labeled with the fluorescent nanocomposite structure.

Additional embodiments and features are set forth in part in the description that follows, and will become apparent to those skilled in the art upon examination of the specification or may be learned by the practice of the disclosed subject matter. A further understanding of the nature and advantages of the disclosure may be realized by reference to the remaining portions of the specification and the drawings, which forms a part of this disclosure.

BRIEF DESCRIPTION OF THE DRAWINGS

The description will be more fully understood with reference to the following figures and data graphs, which are presented as various embodiments of the disclosure and should not be construed as a complete recitation of the scope of the disclosure, wherein:

FIG. 7 is an exemplary embodiment of a Plasmonic Fluor exhibiting a long Stokes shift. Two examples are shown here, one involving a single FRET pair (donor fluorophore and acceptor fluorophore) and one involving a FRET triple in which the intermediate fluorophore (donor2/acceptor1) serves as a bridge between the initial donor fluorophore (donor1) and the final acceptor fluorophore (acceptor 2). In either case, the resulting Plasmonic Fluor can be excited at a wavelength which would excite the shortest wavelength donor fluorophore ($\lambda$EX_D) and will maximally emit at the maximum emission wavelength of the longest wavelength acceptor fluorophore ($\lambda$EM_A).

DETAILED DESCRIPTION

Figure 1:
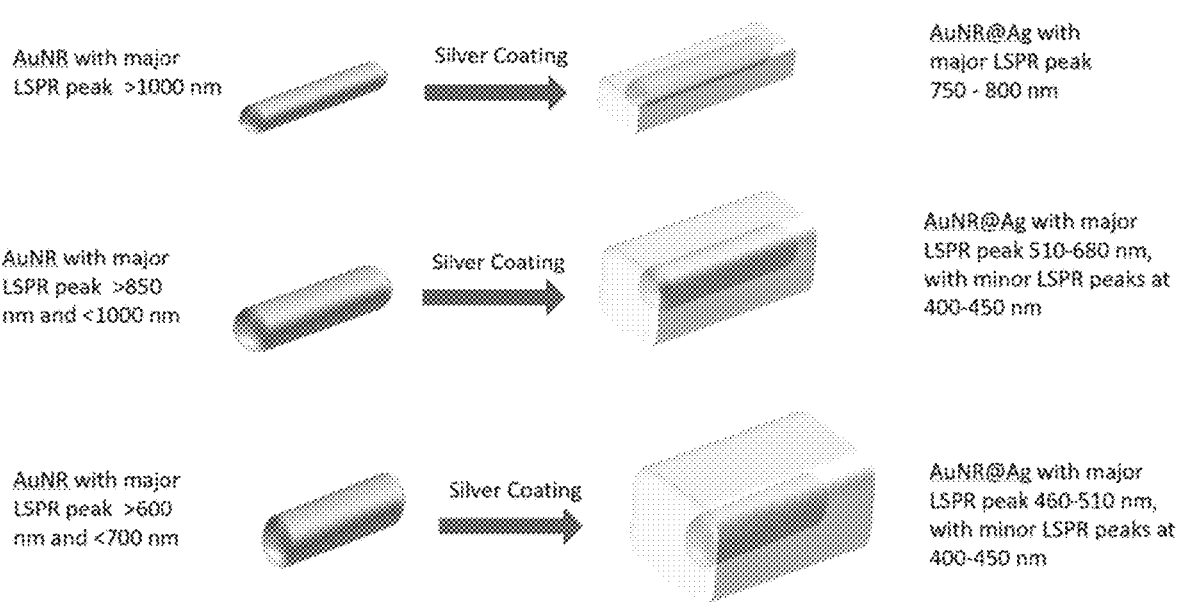
FIG. 1 is an exemplary embodiment of a schematic for creating unique plasmonic core nanoparticles which are then used to create Plasmonic Fluors. In this schematic, a core AuNR with a $\lambda$LSPR above 810 nm can be coated with silver to create an AuNR@Ag with a major $\lambda$LSPR between 650 nm and 800 nm; or a core AuNR with a $\lambda$LSPR above 660 nm and less than 800 nm can be used to create an AuNR@Ag with a major $\lambda$LSPR between 450 nm and 650.
Figure 2:
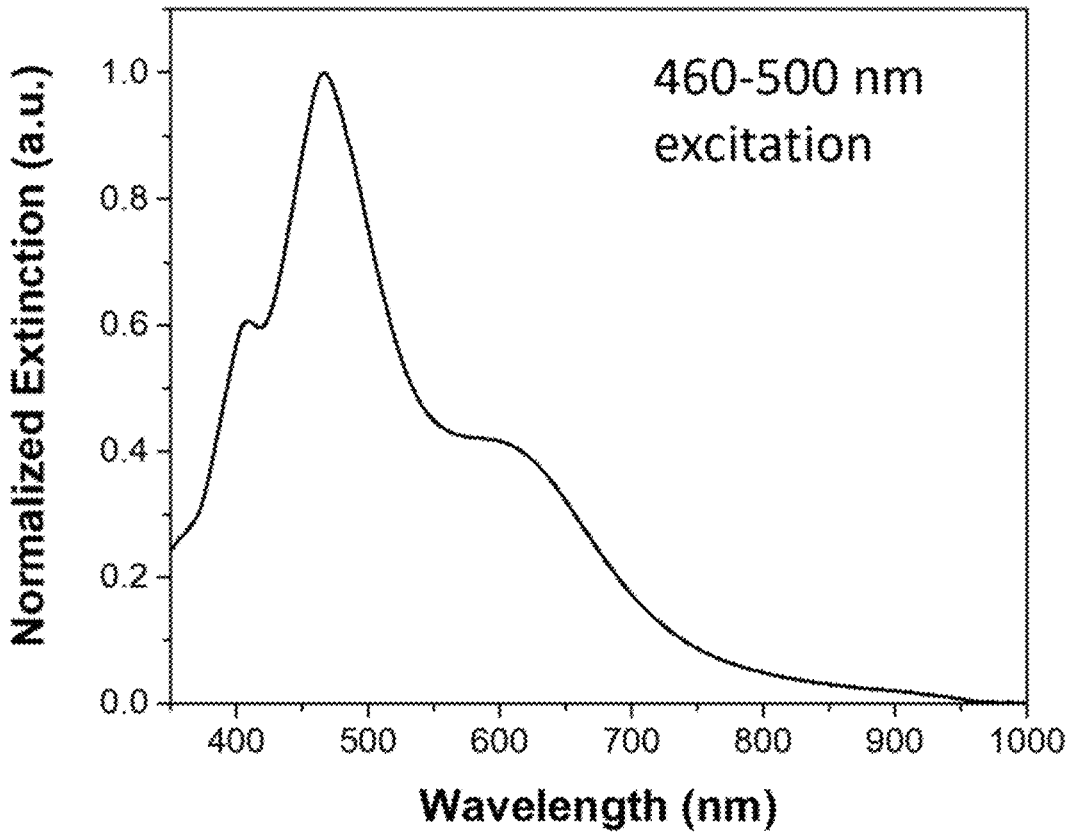
FIG. 2 is an extinction spectrum normalized to 1 at its maximum for an exemplary embodiment of an AuNR@Ag plasmonic particle suitable for enhancing a fluorescent agent which can be excited by light between 460-500 nm such as Cy 2, FITC, and AlexaFluor 488.

The disclosure may be understood by reference to the following detailed description, taken in conjunction with the drawings as described below. It is noted that, for purposes of illustrative clarity, certain elements in various drawings may not be drawn to scale. Several variations of the device are presented herein. It should be understood that various components, parts, and features of the different variations may be combined together and/or interchanged with one another, all of which are within the scope of the present application, even though not all variations and particular variations are shown in the drawings. It should also be understood that the mixing and matching of features, elements, and/or functions between various variations is expressly contemplated herein so that one of ordinary skill in the art would appreciate from this disclosure that the features, elements, and/or functions of one variation may be incorporated into another variation as appropriate, unless described otherwise.

Several definitions that apply throughout this disclosure will now be presented. As used herein, "about" refers to numeric values, including whole numbers, fractions, per-cent-ages, etc., whether or not explicitly indicated. The term "about" generally refers to a range of numerical values, for instance, ±0.5-1%, ±1-5% or ±5-10% of the recited value, that one would consider equivalent to the recited value, for example, having the same function or result.

The term "comprising" means "including, but not necessarily limited to"; it specifically indicates open-ended inclusion or membership in a so-described combination, group, series and the like. The terms "comprising" and "including" as used herein are inclusive and/or open-ended and do not exclude additional, unrecited elements or method processes. The term "consisting essentially of" is more limiting than "comprising" but not as restrictive as "consisting of." Specifically, the term "consisting essentially of" limits membership to the specified materials or steps and those that do not materially affect the essential characteristics of the claimed invention.

As used herein, the term "Plasmonic Fluors" or "fluorescent nanoconstructs" means a composite structure having at least a plasmonic nanostructure at its core, a spacer layer coating the plasmonic nanostructure, and at least one fluorescent agent conjugated on its surface. In some variations, the "Plasmonic Fluors" or "fluorescent nanoconstructs" may further include a scaffold layer and/or a biorecognition element (e.g., MHC, pNMC, Streptavidin, etc.).

As used herein, the term "fluorescent agent" means a dye, a fluorescent probe, or fluorophore that is capable of producing a fluorescent emission upon excitation.

Provided herein are ultrabright fluorescent nanoconstructs, Plasmonic Fluors (PF), which are based on novel silver-containing plasmonic nanostructures. Additionally, disclosed herein are novel Plasmonic Fluors exhibiting large Stokes shifts, the difference between positions of the maxima of the excitation and emission spectra of the fluorophore. Plasmonic Fluors can be conjugated to one or more biorecognition elements and used to enhance existing biological assays. Additionally, these Plasmonic Fluors can enable novel biological assays owing to their exceptional brightness. The Plasmonic Fluor technology disclosed herein can relax instrumentation requirements because they are so much brighter than typical organic fluorophores (i.e. they emit many more photons in a given period of time).

The Plasmonic Fluors exhibit long Stokes shifts allowing significant separation between excitation and emission and are ultrabright. This can enable simpler, less expensive fluorescence detection systems by using broadband excitation sources (e.g. LED's) with longer wavelength detection. Additionally, it may be possible to excite many different fluorophores with the same excitation source and detect each one specifically using different bandpass filters or even monochromators. This is particularly important in highly multiplexed fluorescent assays such as flow cytometry and immunohistochemistry/immunocytochemistry where some fluorophores are used to specifically identify cell populations and other fluorophores are used to provide information about the proteins expressed within these populations.

The relatively large surface area of Plasmonic Fluors allows them to be functionalized with many biorecognition elements. Biorecognition elements may include, but are not limited to MHC, pMHC, streptavidin, neutravidin, or avidin. This leads to a structure with a higher apparent affinity (or avidity) than the biorecognition element in isolation. This is particularly important for cases where one may want to target a complex that has a low affinity for a target but for which multiple targets are present, such as in major histocompatibility complex (MHC) assays for identification of antigen-specific T-cells. Plasmonic Fluors functionalized with peptide-loaded MHC (pMHC) molecules represent the most sensitive reagent available for recognition of T-cell receptors. This is due not only to their incredible brightness but also their ability to be loaded with large amounts of pMHC at a high density.

The present disclosure is directed to an ultrabright fluorescent nanocomposite or Plasmonic Fluor. The fluorescent nanocomposite may include a plasmonic nanostructure having at least one localized surface plasmon resonance wavelength ($\lambda$LSPR), at least one spacer coating, at least one fluorescent agent having a maximum excitation wavelength ($\lambda$EX), and at least one peptide-loaded major histocompatibility complex (MHC) molecule (pMHC). The fluorescent nanocomposite structure has a fluorescent intensity that is at least 500 times greater than a fluorescent intensity of the at least one fluorescent agent alone.

In some examples, the plasmonic nanostructure is a silver-coated gold nanorod nanostructure (AuNR@Ag) which is used as the core particle in an ultrabright fluorescent nanoconstruct. Typically, it is thought that gold is the metal of choice for nanostructures (e.g. gold nanorods (AuNR)) having a major LSPR peak above 600 nm, and, for major LSPR peaks below 600 nm, silver is preferred. For purposes of creating a plasmon-enhanced fluorescent nanoparticle, silver may generally be preferred over gold as it is has a stronger plasmon than gold and can support multiple plasmon modes. Shown here are plasmonic core particles (AuNR@Ag) with tunable LSPR peaks from about 390 nm to about 800 nm, with silver as the metal on the surface and gold nanorods in the center. Silver has a stronger plasmon than gold, and, when incorporated into a Plasmonic Fluor as described, can lead to a higher resultant fluorescence. Silver coating on an AuNR blue shifts the resulting major LSPR peak relative to the major LSPR peak of the original AuNR. Generally, one would select an AuNR with a major LSPR wavelength that is between 100 nm-400 nm longer than the target major LSPR peak of the resulting AuNR@Ag. Because AuNR@Ag nanostructures have multiple plasmon modes owing to the silver, it is demonstrated herein that even these non-dominant plasmon modes can be used to enhance fluorescence of a conjugated fluorophore.

As illustrated in FIG. 1, AuNR@Ag core particles can be created from gold nanorods (AuNR) to have a major LSPR peak between 460 nm and 800 nm by coating a gold nanorod with a higher LSPR wavelength with silver. For example, to create an AuNR@Ag with a major LSPR peak between 750-800 nm, one would start with an AuNR having an LSPR between 1050-1200 nm. Another example is that one would create an AuNR@Ag with a major LSPR peak at 510 nm-680 nm using an AuNR with an LSPR of 850-950 nm. Another example is that one would create an AuNR@Ag with a major LSPR peak at 460 nm-510 nm using an AuNR with a major LSPR peak from 640 nm-700 nm. In addition to the major LSPR peaks, there are significant minor LSPR peaks appearing as low as 395 nm.

In an embodiment, a difference between the at least one $\lambda$LSPR and the $\lambda$EX is less than 75 nm. In at least one example, the major LSPR peak of the AuNR@Ag is within 50 nm of the excitation maximum of the fluorophore to be enhanced. Examples of extinction spectra with dominant peaks identified and examples of fluorophores which would be used to create the resulting Plasmonic Fluors are shown in FIGS. 2-6. In another embodiment, a significant LSPR peak of the AuNR@Ag is within 50 nm of the excitation maximum of the fluorophore to be enhanced. For example, the AuNR@Ag nanostructures corresponding to the spectra shown in FIGS. 2-5 can be used to enhance dyes which are excited with a 405 nm laser, such as Pacific Blue, by relying on the non-dominant LSPR peak of these structures in the 390 nm-410 nm range.

Figure 6:
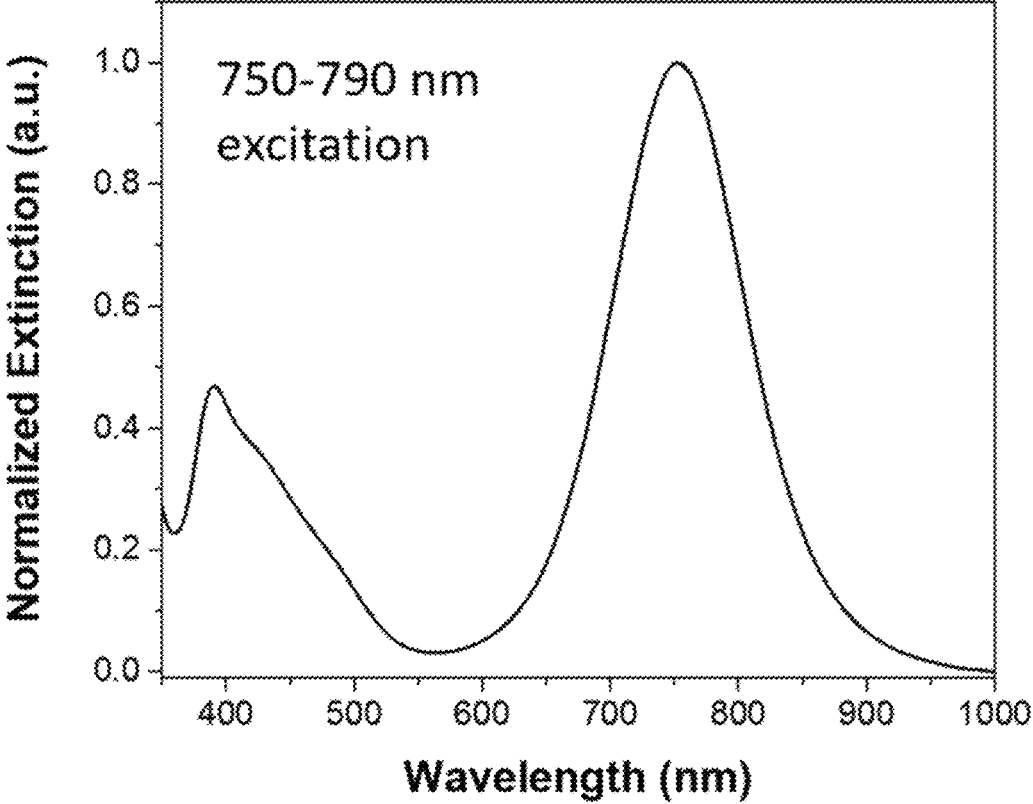
FIG. 6 is an extinction spectrum normalized to 1 at its maximum for an exemplary embodiment of an AuNR@Ag plasmonic particle suitable for enhancing a fluorescent agent which can be excited by light between 750-790 nm such as Cy 7.5, IRDye 800CW, and AlexaFluor 790.

A synthesis for the AuNR@Ag nanostructures whose UV-VIS spectra are shown in FIGS. 2-6 is accomplished by adjusting the ratio of silver nitrate to gold nanorods in a silver overgrowth step. An example procedure for synthesizing an AuNR@Ag with a dominant (major) peak between 750-800 nm as shown in FIG. 6, starting with 380 mL of an AuNR solution in 10 mM cetyltrimethylammonium chloride (CTAC) with an extinction of 0.228 for AuNR with an LSPR of 1050 nm, one adds 15.2 mL of 10 mM silver nitrate. This mixture is heated to 60° C. and 3.8 mL of 100 mM ascorbic acid is added, mixed rapidly, and is incubated for at least 6 hours at 60° C. To make AuNR@Ag with different LSPR peaks, one would follow the procedure above only making changes to the ratios of chemical components (gold nanorods, CTAC, silver nitrate, and ascorbic acid) while starting with an AuNR with a major LSPR wavelength that is between 100 nm-400 nm longer than the target major LSPR peak of the resulting AuNR@Ag. FIGS. 2-6 show spectra for AuNR@Ag with LSPR peaks ranging from ~390 nm to ~800 nm created using the silver overgrowth procedure. Normally, nanoparticles containing silver on their surface are prone to oxidation in aqueous solutions which can degrade the plasmonic properties. The AuNR@Ag used to create fluorescent nanostructures (Plasmonic Fluors) are prepared and coated with a spacer layer as described below within 1 week, which can protect the AuNR@Ag from oxidation. These particles have been stored in aqueous solution for more than 6 months without any notable oxidation or change in the plasmonic properties.

The advantages of using AuNR@Ag as the core plasmonic particle in Plasmonic Fluors are its ease of synthesis, its strong plasmon, and the tunability of its LSPR wavelength in the region of commonly used fluorescent dyes, but it should be noted that Plasmonic Fluors can also be created using a number of other structures capable of supporting a plasmon resonance in the appropriate wavelength regimes including but not limited to: gold nanorods, silver nanocubes, silver or gold nanospheres, bimetallic nanostructures, gold core silver shell nanocuboids, gold or silver nanotubes, gold nanorods, silver nanocubes, silver nanospheres, nanostructures with sharp tips, nanostars, hollow nanostructures, nanocages, nanorattles, nanobipyramids, nanoplates, nanoraspberries.

Figure 9:
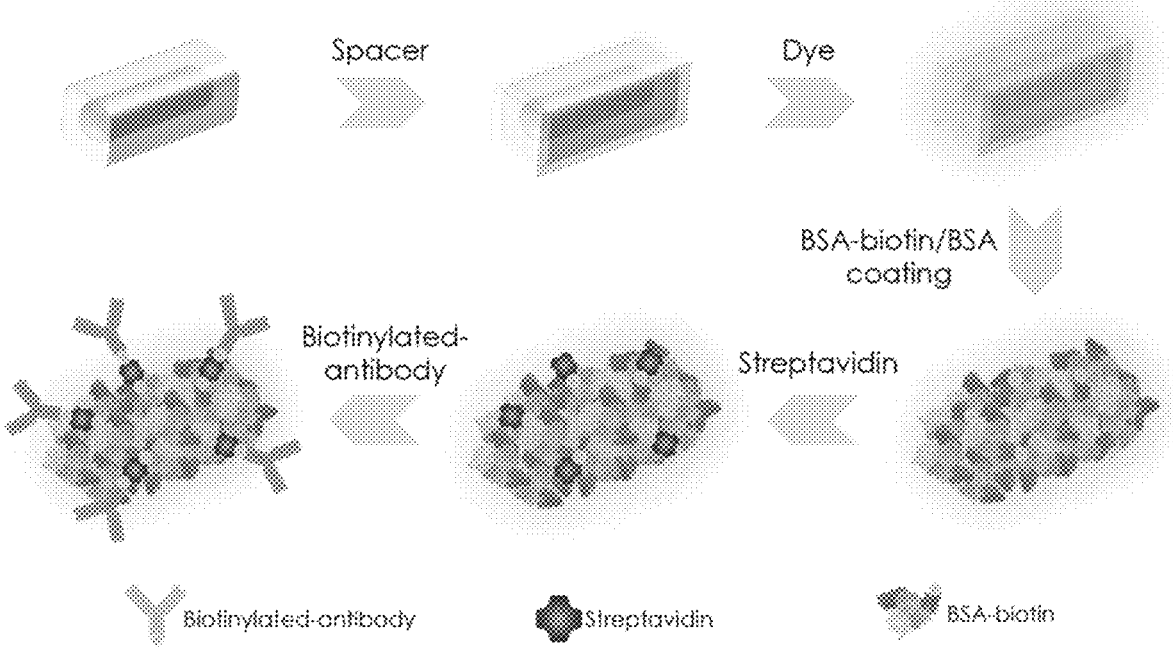
FIG. 9 is an exemplary embodiment of constructing a Plasmonic Fluor using an AuNR@Ag plasmonic core particle. The AuNR@Ag plasmonic core particle is coated with a spacer layer to which a fluorescent dye molecule is then conjugated. This dye-spacer layer is then coated with a functional layer, a combination of biotinylated bovine serum albumin (BSA) and free BSA in this example. Optionally, this biotinylated Plasmonic Fluor can be further modified by attaching streptavidin, which can then, optionally, be modified with a biotinylated antibody.
Figure 10:
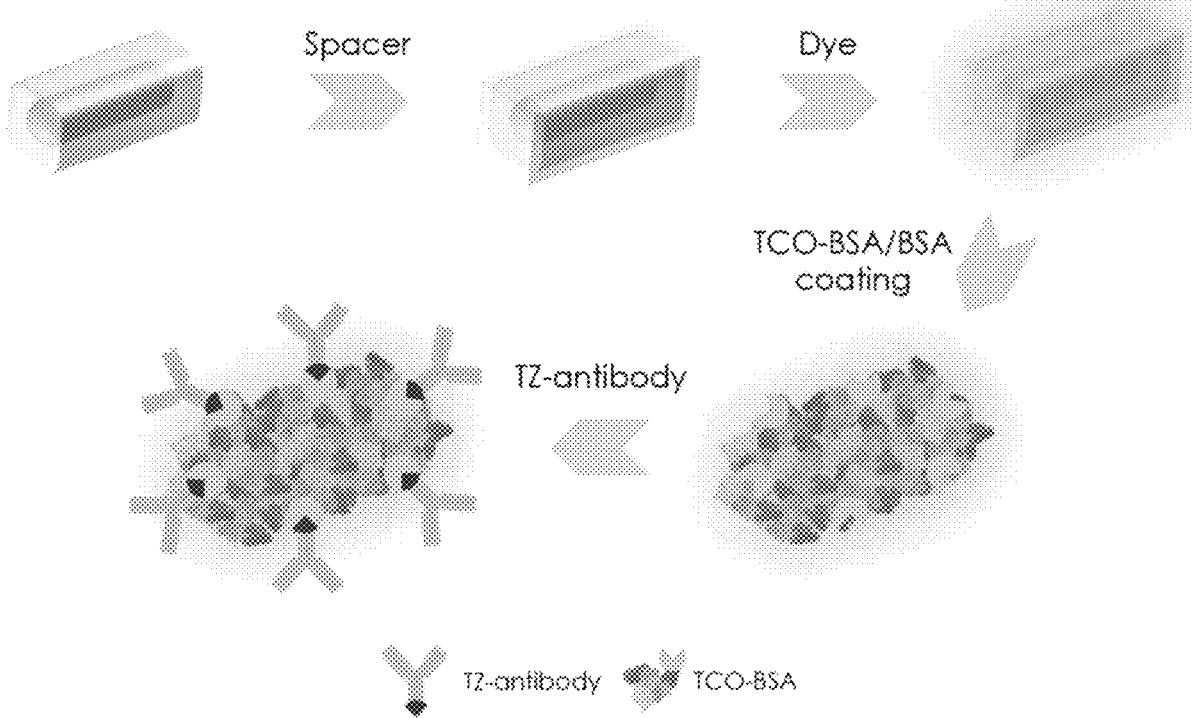
FIG. 10 is an exemplary embodiment of constructing a Plasmonic Fluor using an AuNR@Ag plasmonic core particle wherein the AuNR@Ag plasmonic core particle is coated with a spacer layer to which a fluorescent dye molecule is then conjugated. This dye-spacer layer is then coated with a functional layer, a combination of trans-cyclooctene (TCO) BSA and free BSA in this example. Optionally, this TCO-conjugated Plasmonic Fluor can be further reacted with a tetrazine (TZ)-conjugated antibody. TCO and TZ are just one example of a "click" chemistry pair, but any click pair will work.

In an embodiment, the AuNR@Ag nanostructures serve as the central core for the Plasmonic Fluors. The AuNR@Ag nanostructures may then be coated with at least one spacer coating or spacer layer. For example, the AuNR@Ag nanostructures may be coated with a spacer layer as illustrated in FIG. 9 and FIG. 10. This spacer layer can be any dielectric material which can be coated onto the AuNR@Ag structures and which has a finely controllable thickness. In some embodiments, the spacer coating has a thickness from about 0.5 nm to about 20 nm, about 1 nm to about 10 nm or, about 2 to about 5 nm.

Ideally, the spacer layer has reactive groups that allow conjugation of fluorescent dye molecules, and, after coating, remains stable in solution. An example spacer layer consists of an initiation layer using (3-Mercaptopropyl)trimethoxysilane (MPTMS) which binds the silver surface and allows growth of additional silane layers, and a growth layer containing a mixture of trimethoxy(propyl) silane (TMPS) and (3-Aminopropyl) trimethoxysilane (APTMS). The ratio of TMPS to APTMS can be modified to adjust the coated nanostructure's Zeta potential and density of reactive groups on the surface. To coat the AuNR@Ag particles corresponding to the spectrum shown in FIG. 6 with an optimal spacer thickness, for example, one would first add 400 microliters of MPTMS to a 400 mL solution of AuNR@Ag in 1 mM CTAC wherein the AuNR@Ag have a major LSPR peak of about 760 nm and an extinction of 6-10. This mixture may be incubated for 1 hour at 20° C. under gentle shaking. After 1 hour, 2 mL of APTMS and 2 mL TMPS are added, mixed, and this solution is incubated for 4 hours at 20° C. under gentle shaking. These spacer-coated AuNR@Ag particles are then centrifuged and resuspended in 1 mM CTAC to stop the spacer coating reaction. To coat the AuNR@Ag particles corresponding to the spectrum shown in FIG. 3, as another example, one would follow the exact procedure above but would use AuNR@Ag with a major LSPR peak of about 510 nm and an extinction of 45-50. Using silanes as the basis for the spacer layer is attractive because the thickness is easily controlled in dimension by simply adjusting stoichiometries of reactants.

Spacer-coated AuNR@Ag nanostructures can be conjugated directly to at least one fluorescent agent as illustrated in the second step of FIG. 9 and FIG. 10. In various examples, the at least one fluorescent agent may include at least about 5, at least about 10, at least about 20, at least about 50, at least about 100, at least about 200, at least about 300, at least about 400, or at least about 500 fluorescent agents. Using TMPS and APTMS as the spacer growth layer results in primary amine groups being solvent exposed, and these amine groups are easily functionalized with an amine reactive fluorescent dye, such as, for example, those containing an N-Hydroxysuccinimide (NHS) ester, an isothiocyanate, a Tetrafluorophenyl (TFP) ester, or a Pentafluorophenyl (PFP). For synthesis of a Plasmonic Fluor one would generally choose a single type of fluorescent dye and an appropriate plasmonic nanostructure core such that the excitation maximum of the fluorescent dye is within about 50 nm of a significant LSPR peak of the plasmonic nanostructure. As an example, to label 1 mL of the spacer-coated AuNR@Ag nanostructures corresponding to the spectrum in FIG. 6 at an extinction of 20 and dissolved in 1 mM CTAC with 0.5×phosphate buffered saline, one would add 4 microliters of NHS-sulfo-Cyanine7.5 dissolved in dimethylformamide (DMF) at a concentration of 5 mg/mL and incubate for 12 hours at room temperature. As another example, to label 1 mL of the spacer-coated AuNR@Ag nanostructures corresponding to the spectrum in FIG. 3 at an extinction of 20 and dissolved in 1 mM CTAC with 0.5×phosphate buffered saline, one would add 2 microliters of the dye NHS-MB543 dissolved in dimethylformamide (DMF) at a concentration of 5 mg/mL and incubate for 12 hours at room temperature. The optimal labeling conditions may be found empirically for each dye/nanostructure combination, but should be chosen such that the fluorescence per particle as a function of dye concentration is maximized.

Spectrally unique Plasmonic Fluors having large Stokes shifts can be created by incorporating multiple different types of dye molecules into the Plasmonic Fluor. As illustrated in FIG. 7, it is possible to create a Plasmonic Fluor having a large Stokes shift by incorporating dye molecules into the Plasmonic Fluor which are capable of engaging in Forster Resonance Energy Transfer (FRET). Specifically, one can incorporate fluorescent dyes/agents which form a FRET pair, FRET triplet, FRET quadruplet, or even FRET quintuplet. In a preferred embodiment, the appropriate nanostructure core will have a high molar extinction, and, hence, localized resonant plasmon modes, in the vicinity of the excitation maximum of the first donor dye molecule in the FRET chain (i.e. the dye molecule with the lowest excitation wavelength) and in the vicinity of the light source used for excitation.

In an embodiment, a fluorescent nanocomposite structure may include a plasmonic nanostructure having at least one localized surface plasmon resonance wavelength ($\lambda$LSPR), at least one spacer coating, at least one fluorescent agent having a first maximum excitation wavelength ($\lambda$EX1) and a first maximum emission wavelength ($\lambda$EM1), and at least one fluorescent agent having a second maximum excitation wavelength (@EX2) and a second maximum emission wavelength ($\lambda$EM2). The fluorescent nanocomposite structure can be excited with light at $\lambda$EX1 and can emit light at $\lambda$EM2, such that an intensity of emission at $\lambda$EM2 is greater than an intensity of emission at $\lambda$EM1. Therefore, the at least one fluorescent agent having $\lambda$EX1 is a FRET donor to the at least one fluorescent agent having $\lambda$EX2 which serves as a FRET acceptor. In some examples, a difference between the at least one $\lambda$LSPR and the $\lambda$EX1 is less than 100 nm, less than 75 nm, less than 50 nm, less than 25 nm, or less than 15 nm.

In some embodiments, the fluorescent nanocomposite may further accommodate FRET triples, quadruples, or quintuples. For example, for a FRET triple, the fluorescent nanocomposite may further include at least one fluorescent agent having a third maximum excitation wavelength ($\lambda$EX3) and a third maximum emission wavelength ($\lambda$EM3). The fluorescent nanocomposite structure can be excited with light at $\lambda$EX1 and can emit light at $\lambda$EM3, such that an intensity of emission at $\lambda$EM3 is greater than an intensity of emission at $\lambda$EM1 or $\lambda$EM2.

As illustrated in FIG. 7, the FRET dyes can be conjugated to the same spacer layer that is between 1 nm and 10 nm in thickness, and, preferably, within 2-5 nm. Alternatively, as illustrated in FIG. 7, the FRET dyes can be conjugated to different spacer layers wherein the shortest wavelength donor dye is conjugated to the first spacer layer and the acceptor dye is conjugated to a second spacer layer covering the first and with a thickness between 1 nm and 3 nm. This layer-by-layer scheme can be extended to accommodate FRET triples, quadruples, or quintuples. Additionally, one can combine the mix scheme with the layer-by-layer scheme. For example, one might coat the first layer with the donor dye only and the second layer with a mixture of another dye pair serving as a FRET acceptor for the donor dye and a donor for a longer wavelength acceptor dye.

Figure 3:
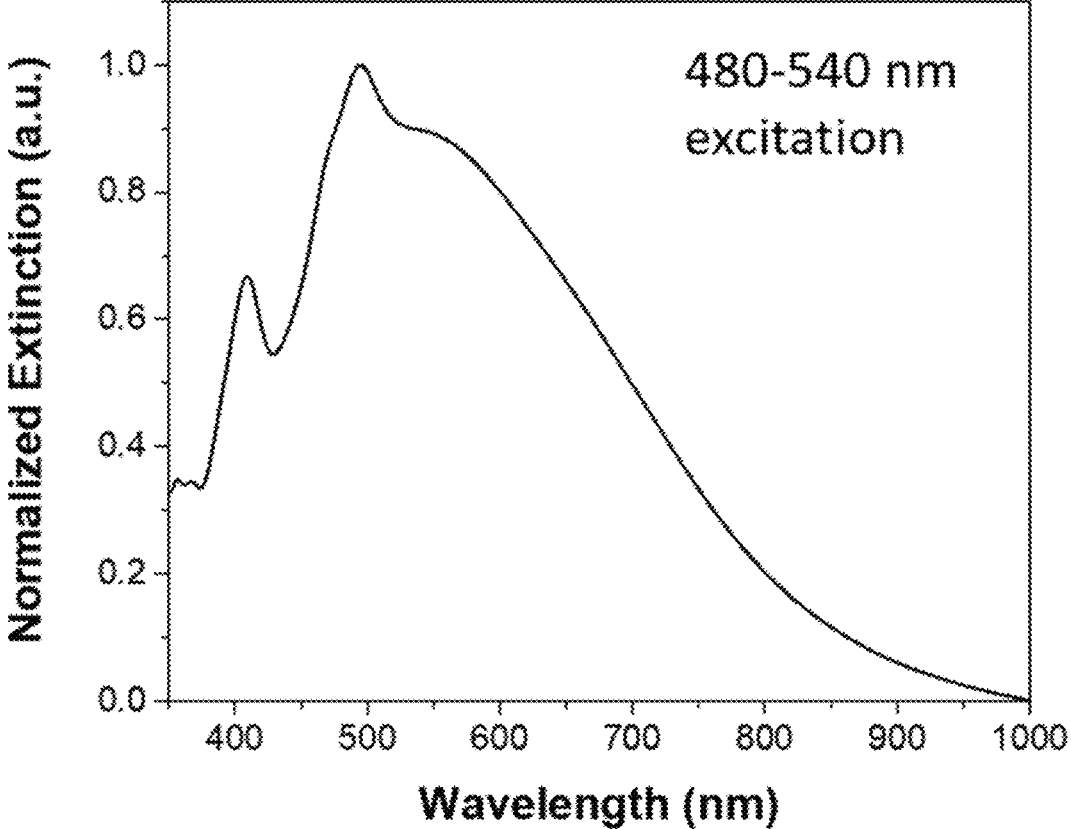
FIG. 3 is an extinction spectrum normalized to 1 at its maximum for an exemplary embodiment of an AuNR@Ag plasmonic particle suitable for enhancing a fluorescent agent which can be excited by light between 480-540 nm such as TRITC, Cy 3, MB543, and AlexaFluor 532.
Figure 4:
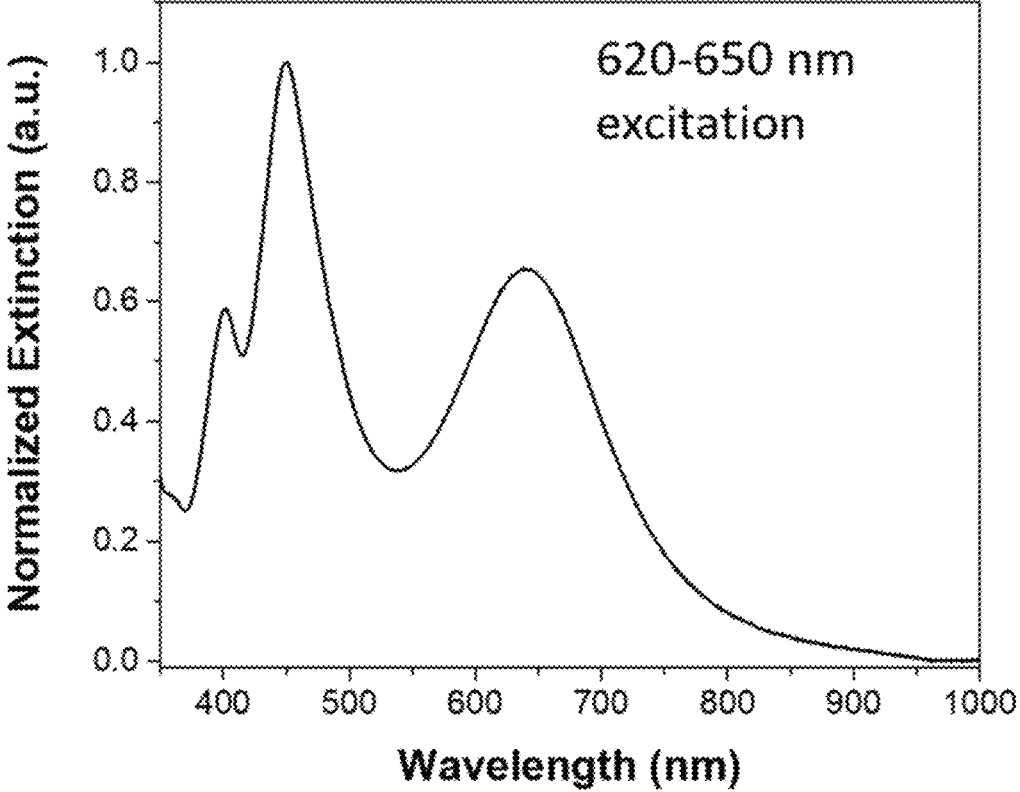
FIG. 4 is an extinction spectrum normalized to 1 at its maximum for an exemplary embodiment of an AuNR@Ag plasmonic particle suitable for enhancing a fluorescent agent which can be excited by light between 620-650 nm such as Cy 5, AlexaFluor 633, and IR Dye 650.
Figure 5:
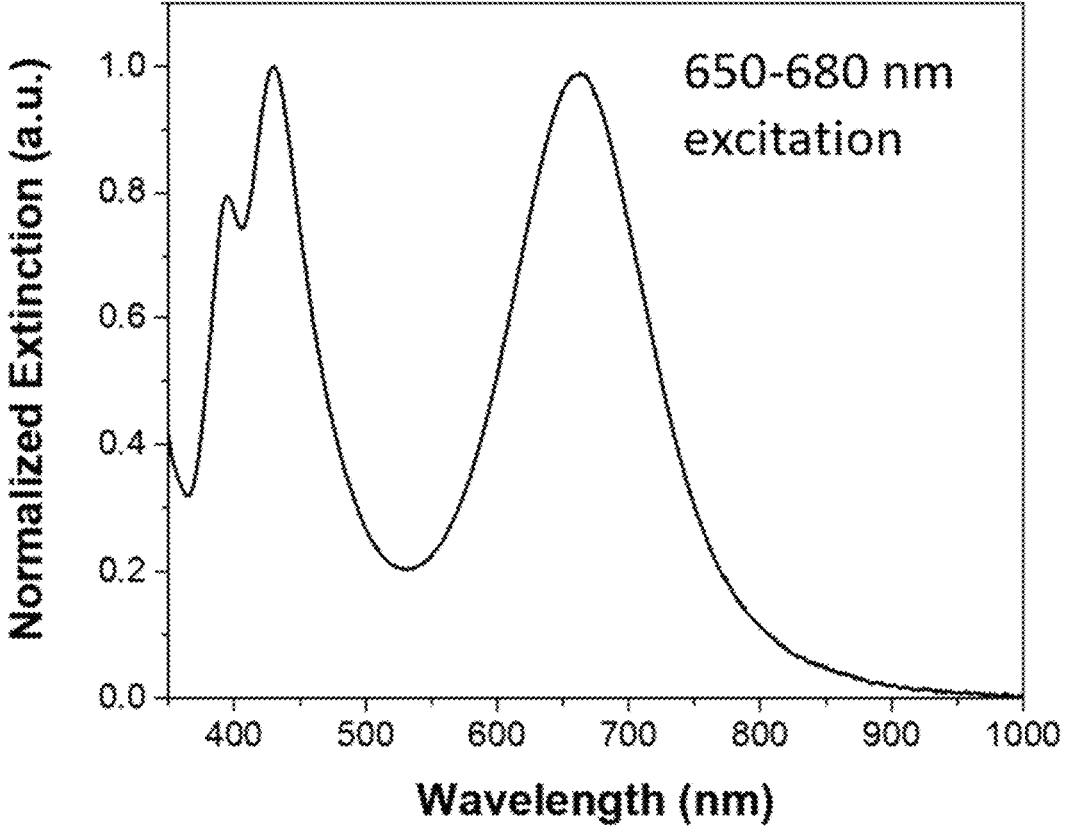
FIG. 5 is an extinction spectrum normalized to 1 at its maximum for an exemplary embodiment of an AuNR@Ag plasmonic particle suitable for enhancing a fluorescent agent which can be excited by light between 650-680 nm such as Cy 5.5, IR Dye 680 LT, and AlexaFluor 680.
Figure 8:
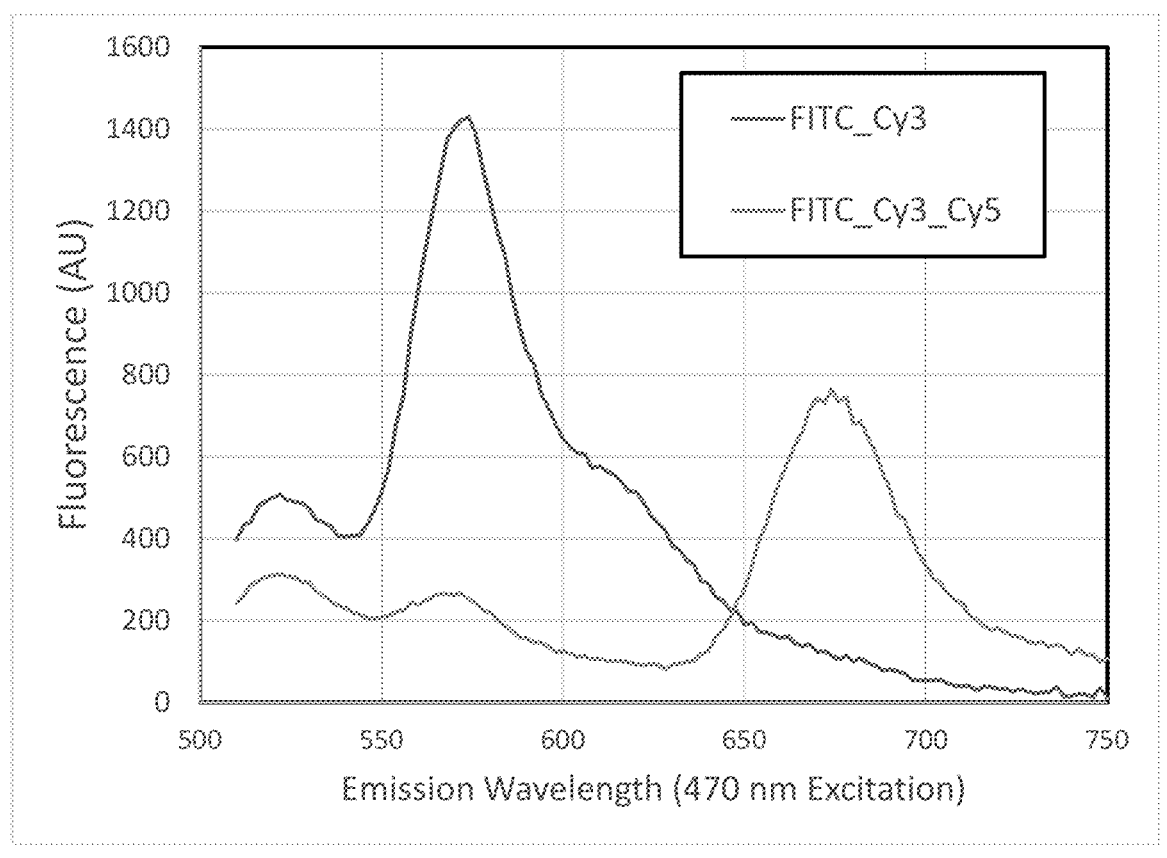
FIG. 8 is a plot of emission spectra of two exemplary embodiments of long Stokes shift Plasmonic Fluors excited by light of 470 nm: one Plasmonic Fluor is coated with the FRET pair FITC-Cy3 and the other Plasmonic Fluor is coated with the FRET triple FITC-Cy3-Cy5. In both cases, significant fluorescence is seen from the longest wavelength acceptor molecule (Cy3 in the FITC-Cy3 pair and Cy5 in the FITC-Cy3-Cy5 triple) and the fluorescence of the donor molecules is suppressed, indicating efficient FRET.

As an example, the spacer-coated AuNR@Ag nanostructures corresponding to the spectrum shown in FIG. 3 were coated in a 1:1 stoichiometric ratio with the FRET pair FITC and Cy3, and the resultant emission spectrum of this Plasmonic Fluor when excited at 470 nm is shown in FIG. 8. When excited at 470 nm, this Plasmonic Fluor shows suppressed emission at FITC's emission maximum around 520 nm and strong emission in the vicinity of Cy3's emission maximum around 570 nm, which are both indications of efficient FRET. In the absence of FITC to serve as a donor molecule, the same Plasmonic Fluor containing Cy3 alone would be very minimally excited by 470 nm light. As an additional example, the spacer-coated AuNR@Ag nanostructures corresponding to the spectrum shown in FIG. 3 were coated in a 1:1:1 stoichiometric ratio with the FRET triplet FITC, Cy3, and Cy5, and the resultant emission spectrum of this Plasmonic Fluor when excited at 470 nm is also shown in FIG. 8. In this embodiment, both FITC and Cy3 fluorescence are suppressed and Cy5 fluorescence is enhanced. In the absence of FITC, the fluorescence of the Cy3-Cy5 particle would be minimal when excited at 470 nm. In the absence of Cy3, the FITC fluorescence would be minimally suppressed and the fluorescence of Cy5 would is minimal due to its poor FRET efficiency with FITC serving as a donor. The optimal labeling stoichiometries are chosen to minimize donor dye fluorescence while maximizing the fluorescence of the ultimate acceptor (i.e. the dye with the longest emission wavelength). One can create a number of spectrally unique, long Stokes shift Plasmonic Fluors by matching an appropriate nanostructure (i.e. one with significant LSPR modes in the vicinity of the shortest wavelength donor's excitation maximum ($\lambda$EX_D) and the excitation source), choosing appropriate FRET dye chains to facilitate resonance energy transfer, and optimizing the labeling stoichiometries to maximize the fluorescence of the Plasmonic Fluor at the maximum emission wavelength ($\lambda$EM_A) of the longest wavelength acceptor dye in the FRET dye chain while suppressing the fluorescence of the donor dyes. Table 1, below, provides examples of dye chain combinations which can be used to create unique Plasmonic Fluors having excitation and emission wavelengths given in column 1. It should be recognized by one skilled in the art that these are non-limiting examples and dyes which are spectrally similar (i.e. have excitation maxima and emission maxima within 15 nm of the dyes listed below) could be substituted to achieve the same effect. For example, Alexa488 could be substituted with FITC or Cy2 without significant difference if the labeling stoichiometries are optimized. As another example, Alexa546 can be substituted with MB543, tetramethylrhodamine, or Cy3. As another example, Alexa633 can be substituted with Cy 5 or IRDye 650.

TABLE 1

| Dye Composition on Plasmonic Fluor for Long Stokes Shift | | | | | |
|---|---|---|---|---|---|
| Ex/Em | Dye 1 | Dye 2 | Dye 3 | Dye 4 | Dye 5 |
| 405/445 | Pacific Blue | | | | |
| 405/530 | Pacific Blue | Alexa488 | | | |
| 405/580 | Pacific Blue | Alexa488 | Alexa546 | | |
| 405/580 | Pacific Orange | | | | |
| 405/615 | Pacific Blue | Alexa488 | Cy3.5 | | |
| 405/615 | Pacific Orange | Cy3.5 | | | |
| 405/660 | Pacific Blue | Alexa488 | Alexa546 | Alexa633 | |
| 405/660 | Pacific Orange | Cy3.5 | Alexa633 | | |
| 405/695 | Pacific Blue | Alexa488 | Alexa546 | Cy5 | |
| 405/695 | Pacific Orange | Cy3.5 | Cy5 | | |
| 405/725 | Pacific Blue | Alexa488 | Alexa546 | Cy5.5 | |
| 405/725 | Pacific Orange | Cy3.5 | Cy5.5 | | |
| 405/780 | Pacific Blue | Alexa488 | Alexa546 | Cy5 | Cy7 |
| 405/780 | Pacific Orange | Cy3.5 | Cy5.5 | Cy7 | |
| 488/530 | Alexa488 | | | | |
| 488/580 | Alexa488 | Alexa546 | | | |
| 488/615 | Alexa488 | Cy3.5 | | | |
| 488/660 | Alexa488 | Alexa546 | Alexa633 | | |
| 488/695 | Alexa488 | Alexa546 | Cy5 | | |
| 488/725 | Alexa488 | Alexa546 | Cy5.5 | | |
| 488/780 | Alexa488 | Alexa546 | Cy5 | Cy7 | |
| 561/580 | Alexa546 | | | | |
| 561/615 | Cy3.5 | | | | |
| 561/660 | Alexa546 | Alexa633 | | | |
| 561/695 | Alexa546 | Cy5 | | | |
| 561/725 | Alexa546 | Cy5.5 | | | |
| 561/780 | Alexa546 | Cy5 | Cy7 | | |
| 640/660 | Alexa633 | | | | |
| 640/695 | Cy5 | | | | |
| 640/725 | Cy5.5 | | | | |
| 640/780 | Cy5 | Cy7 | | | |

In some embodiments, the Plasmonic Fluors may further include a scaffold layer. In an example, after coating with fluorescent dyes, a next step in the preparation of Plasmonic Fluors may be to add a scaffold layer. The scaffold layer serves several purposes: it prevents non-specific adsorption in an immunoassay when using an appropriate blocking reagent; it stabilizes the fluorescent dye-labeled Plasmonic Fluors; and it serves as a base from which one can easily conjugate targeting elements used for biorecognition such as biotin, streptavidin, nucleic acids, or antibodies. The scaffold layer is not absolutely essential because it is possible to attach these targeting elements directly to the spacer layer, but the scaffold layer provides additional labeling versatility and improves the stabilization of the Plasmonic Fluor. One example of a process for creating antibody-coated Plasmonic Fluors using bovine serum albumin (BSA) as a scaffold layer is shown in FIG. 9. In this process, the fluorescent dye-labeled Plasmonic Fluors are incubated with a mixture of biotinylated BSA and native BSA in solution with sonication for about 30 minutes. The labeling density can be easily adjusted by changing the ratio of biotinylated BSA to native BSA from 100% biotinylated BSA to 1% biotinylated BSA. Additionally, it is possible to changing the labeling degree of the biotinylated BSA from 1-10 biotins using an amine-reactive biotinylation reagent such as NHS-PEG4-biotin. The combination of adjusting both the labeling ratio of biotinylated BSA to native BSA and also adjust the degree of biotinylation allows incredible control of the density and distribution of biotin on the surface of the Plasmonic Fluor. The BSA scaffold layer can additionally be cross-linked using glutaraldehyde or another suitable cross-linker to increase stability.

In an embodiment, the Plasmonic Fluors may further include at least one biotin-binding molecule on the spacer coating and/or the scaffold layer. For example, the at least one biotin-binding molecule includes at least about 2, at least about 5, at least about 10, at least about 15, at least about 20, at least about 25, at least about 30, at least about 35, at least about 40, at least about 45, or at least about 50 biotin-binding molecules. Non-limiting examples of the biotin-binding molecule include streptavidin, neutravidin, and avidin. For example, after coating with the BSA/biotinylated-BSA scaffold layer, the Plasmonic Fluors may be functionally reactive towards streptavidin and can be used to specifically detect streptavidin in a biological assay. They can also be coated with streptavidin creating streptavidin-functionalized Plasmonic Fluors, which can be used to specifically detect biotinylated reagents in a biological assay. These streptavidin-coated Plasmonic Fluors can be further modified with another biotinylated reagent, for example antibodies, as shown in FIG. 9. As another example, biotinylated BSA can be replaced with BSA that is functionalized with a "Click" chemistry reactive moiety, for example trans-cyclooctene (TCO) attached to BSA via an NHS-TCO reagent or tetrazine (Tz) attached to BSA via an NHS-tetrazine, and the scaffold layer can be formed using a mixture of BSA:BSA-TCO or BSA-Tz as illustrated in FIG. 10. Those skilled in the art will recognize that any Click reactive pair can be used in lieu of TCO/TZ, including but not limited to azide-alkyne pair in copper-catalyzed Click reactions. Additionally, it is possible to conjugate targeting elements (e.g. streptavidin, antibodies, nucleic acids, etc.) to a click-functionalized Plasmonic Fluor by incubating the click-functionalized Plasmonic Fluor with a targeting element labeled with a complementary click-moiety as illustrated in FIG. 10.

In an embodiment, the Plasmonic Fluors may further include at least one peptide-loaded MHC (pMHC) molecule on its outer surface. In various examples, the pMHC molecule may be biotinylated and the biotinylated pMHC may be attached to a biotin-binding molecule on the spacer coating and/or the scaffold layer. The at least one biotinylated pMHC molecule may include at least about 2, at least about 4, at least about 8, at least about 12, at least about 16, at least about 20, at least about 24, at least about 28, at least about 32, at least about 36, at least about 40, or at least about 48 pMHC molecules. Plasmonic Fluors conjugated with pMHC represent a very attractive platform for MHC tetramer assays or tetramer stains which are used for identifying antigen-specific T-cells which contain T-cell receptors (TCRs) that specifically recognize the peptide loaded in the pMHC. The standard reagent used for identifying antigen-specific T-cells in a so-called MHC-tetramer assay (a.k.a. tetramer stain) is a fluorescently labeled streptavidin bound to four biotinylated-pMHC molecules. A single pMHC-receptor complex has a relatively weak affinity, so, by combining four pMHC molecules in a single complex by linking them through a streptavidin, the avidity, and, hence, the apparent affinity is increased. This concept has been further extended by linking multiple of these MHC-tetramer molecules to create, for example, pMHC dodecamers. Another alternative is to attach pMHC to fluorescently labeled dextran to create so-called dextramers. Disclosed herein are methods and compositions for creating a Plasmonic Fluor decorated with many MHC molecules, preferably 8-40 or more.

The resulting composition has several advantages over existing materials: 1) the Plasmonic Fluor itself is at least 50×brighter than traditional fluorophores, including PE, resulting in a higher signal; 2) the presence of multiple pMHC molecules (at least 12) provides a pMHC-decorated Plasmonic Fluor with a very high avidity/apparent affinity;

and 3) the physical size of the pMHC-decorated Plasmonic Fluor (>50 nm in longest dimension) allows binding of cell-surface receptors over a larger area which means that T-cells with lower densities of receptors can be detected. In some embodiments, the Plasmonic Fluor has a fluorescent intensity that is at least 50 times greater, at least 100 times greater, at least 200 times greater, at least 300 times greater, at least 400 times greater, or at least 500 times greater than the fluorescent intensity of the fluorescent agent alone.

Figure 11:
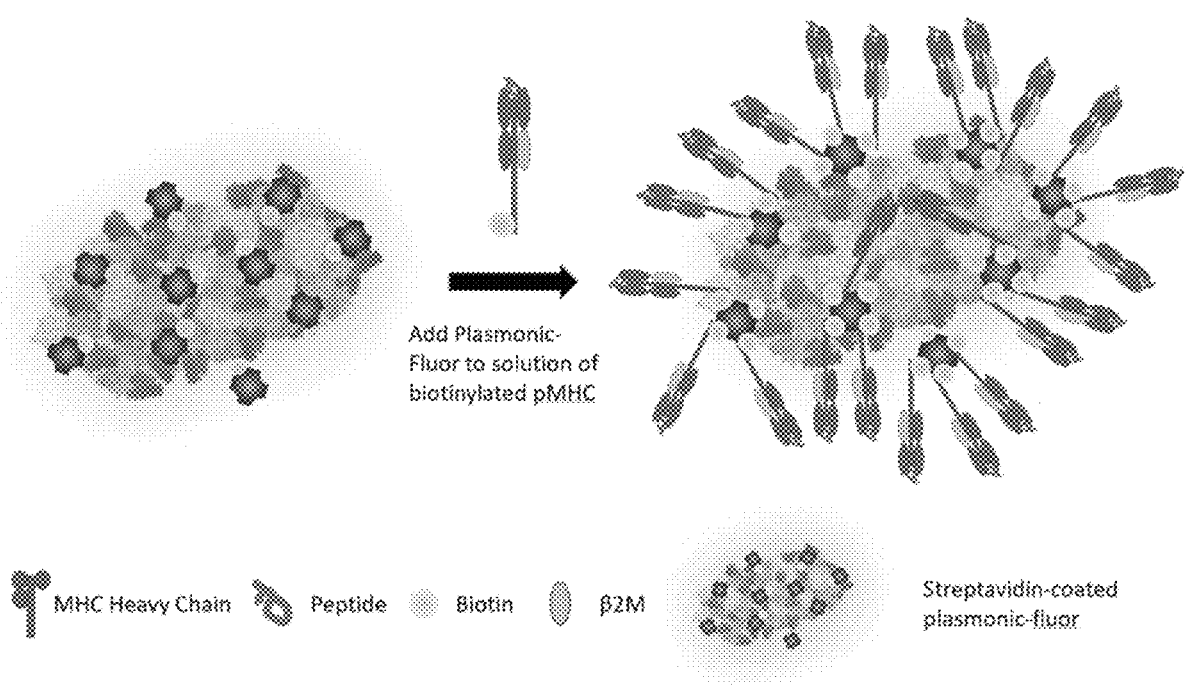
FIG. 11 is an exemplary embodiment of a pMHC-decorated Plasmonic Fluor and a method of creating the same. A streptavidin-conjugated Plasmonic Fluor can be used to create a pMHC-decorated Plasmonic Fluor by adding the streptavidin-conjugated Plasmonic Fluor to a solution containing an excess of biotinylated pMHC.

In an example embodiment, a pMHC-decorated Plasmonic Fluor can be assembled by combining a streptavidin-coated Plasmonic Fluor with biotinylated-pMHC by adding the streptavidin-conjugated Plasmonic Fluors to a solution containing a molar excess of biotinylated pMHC molecules, wherein the molar excess is determined relative to the molar concentration of streptavidin in the solution containing streptavidin-conjugated Plasmonic Fluors as illustrated in FIG. 11. The pMHC-decorated Plasmonic Fluors can be separated from free pMHC by centrifugation. Excess free biotin may be added after the reaction prior to the centrifugation to ensure that all biotin binding sites are occupied, thereby minimizing any possible cross-linking and aggregation. The density of the pMHC on the surface of the Plasmonic Fluors in this design may be easily varied by simply altering the ratio of biotinylated BSA to BSA used in the preparation of the Plasmonic Fluors or by altering the degree of biotinylation of the BSA or both. This ultimately has the effect of changing the number of streptavidins present on the surface of the Plasmonic Fluor. It should be recognized that the BSA coating in this context serves as a scaffold and could be substituted for a number of different proteins and other polymers that could serve a similar function. Additionally, biotin can be incorporated directly into the silane spacer layer using (e.g. biotin-PEG-silane) or biotin-PEG-nhs ester can be added through exposed amines similar to how the fluorescent dyes are conjugated. In this scenario, the streptavidin can be conjugated directly through these biotins, bypassing the need for a scaffold.

In another embodiment, a pMHC-decorated Plasmonic Fluor can be assembled by combining a Plasmonic Fluor containing reactive click chemistry moieties with pMHC labeled with the complementary click moiety (e.g. Plasmonic Fluors labeled with TCO-PEG-NHS ester and pMHC labeled with Tetrazine-PEG-NHS ester). In this scenario the PEG acts as a spacer to improve conjugation efficiency, but may be omitted. The PEG may be between 2 and 24 monomeric units in length). In this "clicked" pMHC embodiment, a Plasmonic Fluor is first coated with a mixture of TCO-labeled BSA and free BSA wherein the percentage of TCO-BSA can range from 100% to about 5%, and is, ideally, between 80% and about 10%. This TCO-Plasmonic Fluor can then be incubated with a molar excess of tetrazine-labeled pMHC molecules. The density of the pMHC on the surface of the Plasmonic Fluors can be varied by simply varying the ratio of TCO-BSA to BSA. In another embodiment, the MHC molecule is engineered to have an unpaired cysteine at the C-terminus or a solvent exposed loop, and a reactive click moiety is added to the MHC molecule through a sulfhydryl reactive reagent (e.g. maleimide-PEG-Tz or maleimide-PEG-TCO). This can then be conjugated to a complementary functionalized Plasmonic Fluor.

Normally, MHC molecules are expressed in bacterial culture and include a biotinylation tag, such as BSP or AviTag. After purification and refolding of the MHC molecules, this tag is modified with a biotin ligase, such as BirA, wherein the biotin ligase site-specifically adds a biotin molecule. With a Click version of the Plasmonic Fluor it is possible to directly link an appropriately modified MHC molecule. Using genetic code expansion technology, it is possible to introduce non-canonical amino acids into proteins site-specifically. Using this strategy, one can replace at least one native amino acid in the MHC molecule at, for example, the C-terminal region, with a non-canonical amino acid containing a Click reactive moiety. An example amino acid which can react with Tz-functionalized Plasmonic Fluors is TCO*-L-lysine (TCO*-Lys), but any amino acid with a Click functional group, such as azido- or alkyne-containing amino acids, can be used if a Plasmonic Fluor is functionalized with the appropriate complementary reactive unit. To incorporate the Click-reactive amino acid into the MHC molecule, one would simply substitute a native codon at the desired modification site with a rare codon, for example the amber (TAG) stop codon, and express the protein along with an additional tRNA-tRNA synthetase pair (tRNA-RS) that is orthogonal to the host translational machinery. The active site of the tRNA synthetase enzyme is engineered to only accept the specific click-functionalized, non-canonical amino acid, which is incorporated into a tRNA that recognizes the rare codon. The Click-functionalized, non-canonical amino acid is simply added to the growth medium and thereby incorporated into the MHC protein at a specific site. An advantage of this approach is the elimination of adding a biotin ligase recognition sequence to the MHC, and elimination of the ligation reaction using the biotin ligase. This same approach can be applied to Click-functionalize antibodies and other biologically expressed molecules and then subsequently conjugating them to a complementary Click-functionalized Plasmonic Fluor.

Further provided herein is a method of identifying T-cells with specific T-cell receptors. In an embodiment, the method may include providing a sample containing T-cells, contacting the sample containing T-cells with a fluorescent nanocomposite structure, spatially separating the T-cells, exciting the fluorescent nanocomposite structure with a wavelength of light that will induce fluorescence emission, and detecting the T-cells that are labeled with the fluorescent nanocomposite structure. In some examples, the T-cells may be spatially separated using flow cytometry.

The fluorescent nanocomposite structure may contain at least one major histocompatibility complex (MHC) molecule loaded with a peptide (pMHC) that can specifically bind to T-cells containing receptors specific to the peptide. In some embodiments, the fluorescent nanocomposite structure comprises a plasmonic nanostructure having at least one localized surface plasmon resonance wavelength ($\lambda$LSPR), at least one spacer coating, and at least one fluorescent agent having a maximum excitation wavelength. The fluorescent nanocomposite structure has a fluorescent intensity that is at least 500 times greater than a fluorescent intensity of the at least one fluorescent agent alone.

EXAMPLES

Example 1: Preparation of
Streptavidin-Functionalized Plasmonic Fluor 1 mL of Plasmonic Fluor labeled with a fluorescent agent at extinction 20 at its LSPR wavelength was centrifuged to form a pellet. 990 μL of the supernatant was removed. In a separate microcentrifuge tube, 200 μL of biotinylated-BSA solution (at least 100×molar excess relative to Plasmonic Fluor to be coated) was added in an appropriate buffer (e.g. 50 mM carbonate-bicarbonate buffer at pH 9). The entirety of the Plasmonic Fluor pellet was transferred to the solution of biotinylated-BSA and sonicated in a water bath for 30 minutes. It was removed from the sonic water bath and the solution was incubated in 4° C. for 15 hours. The solution of biotinylated-BSA coated Plasmonic Fluor was centrifuged to form a pellet and then all but 10 µL of the supernatant was removed. In a separate microcentrifuge tube 200 µL of streptavidin solution (at least 50×molar excess relative to the Plasmonic Fluor to be coated) was added in an appropriate buffer (e.g. 50 mM carbonate-bicarbonate buffer at pH 9). The entirety of the pellet biotinylated-BSA coated Plasmonic Fluor was transferred to the streptavidin solution and incubated for 2 hours. This solution was centrifuged to form a pellet and the supernatant was removed. It was Resuspended in an appropriate buffer (e.g. 50 mM carbonate-bicarbonate buffer at pH 9 with 1% BSA) solution. This was repeated two more times to remove unbound streptavidin.

Example 2: Construction of a
pMHC-Functionalized Plasmonic Fluor

A streptavidin-functionalized Plasmonic Fluor (Strep-PF) like that of Example 1 was adjusted to an extinction of 20 at its LSPR wavelength and 1 mL was removed and placed in a microcentrifuge tube. This solution was centrifuged to pellet the Strep-PF and about 990 µL of the supernatant was removed. In another microcentrifuge tube, 400 µL of 8 µM (368 µg/mL peptide-MHC I complex or 232 µg/mL peptide-MHC II) solution was added in compatible buffer, for example 1×PBS (phosphate buffered saline) pH 7.4 on ice. The entirety of the centrifuged Strep-PF pellet was transferred to the MHC-peptide complex solution and this was vortexed for 10 s and then incubated for 2 hours at 4° C. The reaction can be used directly or optionally blocked by adding a molar excess of biotin and then used.

Example 3: Plate-Based Assay Confirming
Plasmonic Fluor is Functionalized with pMHC A simple method for confirming that Plasmonic Fluor has been conjugated with pMHC was to perform an immunoassay against an MHC moiety. This was done by coating a microtiter plate with a 1 µg/mL concentration of antibody specific to an MHC moiety, either anti-β2-microglobulin or anti-MHC Class-specific antibody, in PBS. The plate was then blocked with a suitable blocking agent (e.g. 1% BSA in 1×PBS), and washed with a suitable washing agent (e.g. 1×PBS containing 0.05% Tween 20). An amount of solution containing Plasmonic Fluor conjugated to pMHC was then incubated in the plate for 10 minutes, removed, and the plate was washed with a suitable washing agent. The Plasmonic Fluor fluorescence on the plate surface was then detected using a suitable reader and compared to a control well of the microtiter plate that was not coated with antibody specific to an MHC moiety. Because the MHC complex will dissociate rapidly when the peptide is not bound, this procedure ensured the pMHC complex was functionally active.

Example 4: Identifying a Population of T-Cells
Capable of Recognizing a Specific Peptide Cells of interest (e.g. CD8-positive T-cells) were prepared and $2\times10^6$ cells were added to a microcentrifuge tube of well of a 96-well microtiter plate. The volume was adjusted to 200 µL with an appropriate cell staining buffer (e.g. 1×PBS with 5% fetal bovine serum). 2 µL of the pMHC-functionalized Plasmonic Fluor solution was added, like that in Example 2 wherein the pMHC contained the peptide of interest and incubated for 30 minutes on ice in the dark. The cells were washed twice for staining buffer and resuspended in 200 µL of staining buffer. The cells were analyzed using a flow cytometer with appropriate settings to detect the specific fluorescent signal of the Plasmonic Fluor used. A titration of the concentration of the pMHC-functionalized Plasmonic Fluor may be necessary for optimal performance.

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should be interpreted as illustrative and not be taken as limiting the scope of the invention. The following claims are intended to cover all generic and specific features described herein, as well as all statements of the scope of the present method and composition, which, as a matter of language, might be said to fall therebetween.

What is claimed is:

1. A fluorescent nanocomposite structure comprising:
   a plasmonic nanostructure having at least one localized surface plasmon resonance wavelength (λLSPR);
   a spacer layer coating the plasmonic nanostructure;
   at least one fluorescent agent having a first maximum excitation wavelength (λEX1) and a first maximum emission wavelength (λEM1) conjugated on the spacer layer; and
   at least one fluorescent agent having a second maximum excitation wavelength (λEX2) and a second maximum emission wavelength (λEM2) conjugated on the spacer layer,
   wherein the fluorescent nanocomposite structure can be excited with light at λEX1 and can emit light at λEM2, and
   wherein an intensity of emission at λEM2 is greater than an intensity of emission at λEM1, and
   wherein the at least one fluorescent agent having λEX1 is a FRET donor to the at least one fluorescent agent having λEX2 which serves as a FRET acceptor.

2. The fluorescent nanocomposite structure according to claim 1, wherein a difference between the at least one λLSPR and the λEX1 is less than 75 nm.

3. The fluorescent nanocomposite structure according to claim 1, further comprising; at least one fluorescent agent having a third maximum excitation wavelength (λEX3) and a third maximum emission wavelength (λEM3) conjugated on the spacer layer, wherein the fluorescent nanocomposite structure can be excited with light at λEX1 and can emit light at λEM3, and wherein an intensity of emission at λEM3 is greater than an intensity of emission at λEM1 or λEM2.

4. The fluorescent nanocomposite structure according to claim 1, wherein the spacer layer has a thickness from about 1 nm to about 20 nm.

5. The fluorescent nanocomposite structure according to claim 1, wherein the spacer layer has a thickness from about 1 nm to about 15 nm.

6. The fluorescent nanocomposite structure according to claim 1, wherein the spacer layer has a thickness from about 1 nm to about 10 nm.

7. The fluorescent nanocomposite structure according to claim 1, wherein the spacer layer has a thickness from about 1 nm to about 5 nm.

8. The fluorescent nanocomposite structure according to claim 1, wherein the spacer layer has a thickness from about 2 nm to about 5 nm.

* * * * *